Figure 1:
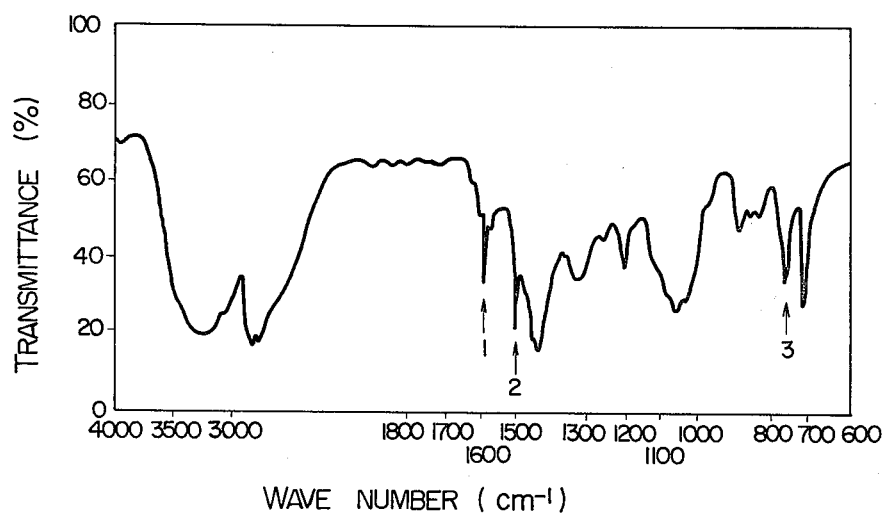

United States Patent [19]

Hamanaka et al.

[11] 4,385,184

[45] May 24, 1983

[54] CATIONIC SURFACE ACTIVE AGENTS

[76] Inventors: Hiroyoshi Hamanaka, Yachiyo; Tadao Goto, Chiba; Kazuichi Umeda, Tokyo; Takashi Amagai, Kisarazu; Takashi Shishito, Ichihara, all of Japan

[21] Appl. No.: 236,950

[22] Filed: Feb. 23, 1981

[30] Foreign Application Priority Data

Dec. 1, 1980 [JP] Japan ................. 55-169264

[51] Int. Cl.$^3$ .................. C07C 85/06; C07C 91/38
[52] U.S. Cl. ...................... 564/286; 564/287; 549/551
[58] Field of Search ............. 564/290, 286, 288, 287, 564/285; 260/348.44

[56] References Cited

U.S. PATENT DOCUMENTS

| | | | |
|---|---|---|---|
| 3,055,939 | 9/1962 | Cavallito et al. | 564/290 |
| 3,079,436 | 2/1963 | Hwa | 564/290 |
| 3,349,032 | 10/1967 | Krieg | 564/286 |
| 3,518,308 | 6/1970 | Daum et al. | 564/287 |
| 3,769,346 | 10/1973 | Boissier et al. | 564/286 |
| 3,936,503 | 2/1976 | Miller et al. | 564/290 |
| 3,992,432 | 11/1976 | Napier | 260/465.1 |
| 4,166,073 | 8/1979 | Baumann | 564/290 |

OTHER PUBLICATIONS

Dockx, Synthesis, p. 441, (1973).
Makosza, Pure & Appl. Chem., vol. 43, p. 439 (1975).
Gokel et al., Synthesis, (1976), p. 168.
Jones, Aldrichimica Octa, vol. 9, #3, pp. 35-45 (1976).

*Primary Examiner*—James H. Reamer
*Attorney, Agent, or Firm*—Sheridan Neimark; Karl W. Flocks

[57] ABSTRACT

Cationic surface active agents in which nitrogen atoms are attached to both ends of a long-chain alkylene group or polyoxyalkylene group having at least 6-24 carbon atoms in the molecule, at least one of said nitrogen atoms constituting a quaternary ammonium structure, have also at least one hydroxyphenethyl group bonded to at least one of the two nitrogen atoms. These cationic surface active agents can serve as an accelerator which catalytically promotes changes in a chemical and/or physical change process involving a hydrolyzing, deacidizing or extracting operation using an aqueous solution of an alkaline metal hydroxide or an alkaline earth metal hydroxide.

11 Claims, 2 Drawing Figures

CATIONIC SURFACE ACTIVE AGENTS

This invention relates to cationic surface active agents. More particularly, the invention is intended to provide the specific cationic surface active agents in which nitrogen atoms are attached to both ends of a long-chain alkylene group or polyoxyalkylene group having, in all, 6 to 24 carbon atoms, at least one of said nitrogen atoms constituting a quaternary ammonium structure, and also at least one hydroxy phenethyl group is bonded to at least one of the two nitrogen atoms. These cationic surface active agents find peculiar use as accelerators which catalytically act to promote changes in a chemical and/or physical change process involving a hydrolyzing, deacidizing or extracting operation using an aqueous solution of an alkaline metal hydroxide or an alkaline earth metal hydroxide.

It has been long known that the cationic surface active agents comprising one nitrogen atom principally constituted from a quaternary ammonium salt are useful as micellar catalysts or phase transfer catalysts, and the structures and preparation process of such cationic surface active agents are also generally know. The following are examples of prior art literature.

J. Dockx, Synthesis, (1973), 441
M. Makosza, Pure and Appl. Chem., 43, 439 (1975)
G. W. Gokel, H. D. Durst, Synthesis, (1976), 168

However, there has yet been known no cationic surface active agent of an $\alpha,\omega$-type dihydrophilic group structure like the products of this invention, and no light has ever been shed on the fact that the cationic surface active agents having an N- and/or N'-hydroxyphenethyl-substituted $\alpha,\omega$-type dihydrophilic group structure have the disposition together around the interface and, owing to this property, they prove to be very effective micellar catalysts or phase transfer catalyst which is minimized in escape.

Figure 2:
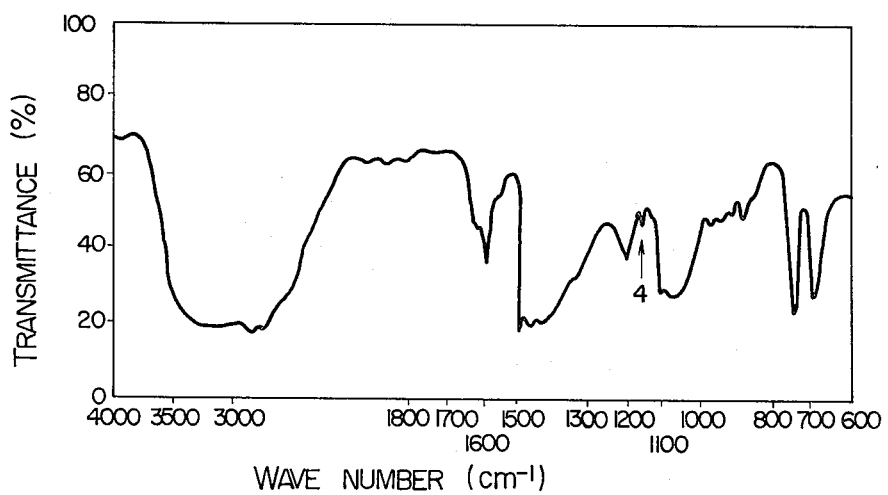

In the accompanying drawings, FIG. 1 is an IR spectrum of N-hydroxyethyl-N,N'-di(2-hydroxyphenethyl-)undecylenediamine which is an intermediate product in Example 1, in which numerals 1, 2 and 3 show the absorption bands indicating presence of benzene nucleus. FIG. 2 is an IR spectrum of a hydrochloric acid neutralized product of (methyl=2-hydroxyphenethyl-)aminoundecyl=methyl=2-hydroxyethyl=2-hydroxyphenethyl=ammonium=chloride which is the final product in Example 1. Numeral 4 shows an absorption band of quaternary nitrogen.

As a result of further diversified studies, the present inventors have first reached an invention for preparation of cationic surface active agents having a quaternary ammonium structure represented by the following general formula I:

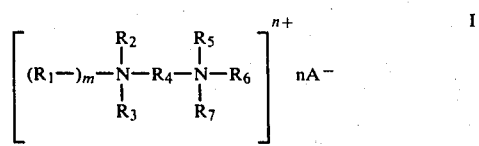

(wherein $R_1$ is hydrogen, or alkyl or hydroxyalkyl having 1-8 carbons, hydroxypolyoxyalkyl having 2-8 carbons, alkylphenyl or phenylalkyl having 7-8 carbons, phenyl, methylbenzyl; or glycidyl group, $R_2$, $R_3$, $R_5$, $R_6$ and $R_7$ are each alkyl or hydroxyalkyl of 1-8 carbons, hydroxypolyoxyalkyl of 2-8 carbons, alkylphenyl or phenylalkyl of 7-8 carbons, phenyl, methylbenzyl or glycidyl group; $R_4$ is an alkylene or polyoxyalkylene group having 6-24 carbon atoms in total, m is 0 or 1, n is 1 or 2, and at least one of $R_1$, $R_2$, $R_3$, $R_5$, $R_6$ and $R_7$ is a hydroxyphenethyl group; A is an anion of halide or an organic or inorganic oxyacid residue) by (i) reacting 1-4 moles of styrene oxide with 1 mole of at least one of the $\alpha,\omega$-polyoxyalkylenediamines (the total carbon number of the alkylene or polyoxyalkylene group being 6-24) which is either unsubstituted or substituted with N- and/or N'-alkyl, N-and/or N'-aryl, N- and/or N'-alkylphenyl, N- and/or N'-phenylalkyl, N- and/or N'-methylbenzyl, N- and/or N'-hydroxyalkyl and/or N- and/or N'-hydroxypolyoxyalkyl (the carbon number per one substituted being 1-8) having at least one NH group in the molecule, and then further reacting the resultant product with 1-5 moles of at least one of the alkyl halides, hydroxyalkyl halides, hydroxypolyoxyalkyl halides, epoxyalkyl halides and alkyl esters of inorganic acids (the carbon number of the alkyl group being 2-8) at such a reaction molar ratio as to induce quaternarization of at least one nitrogen atom, or reacting 1-12 moles of at least one of formaldehyde, ethylene carbonate and alkylene oxide (the carbon number of the alkylene group being 2-8) with 1 mole of at least one of said diamines and further reacting the resultant product with 1-4 moles of at least one of the alkyl halides, hydroxyalkyl halides, hydroxypolyoxyalkyl halides, epoxyalkyl halides and alkyl esters of inorganic acids (the carbon number of the alkyl group being 1-8), or reacting 1-2 moles of at least one of the organic or inorganic acids and alkyl esters thereof with 1 mole of at least one of said diamines and successively reacting the resultant product with 1-20 moles of at least one of formaldehyde, ethylene carbonate and alkylene oxide (the carbon number of the alkylene group being 2-8), or (ii) by reacting 1 mole of at least one of the alkylene dihalides and polyoxyalkylene dihalides (the total carbon number of the alkylene or polyoxyalkylene group being 6-24) with total 2 moles of a mixture consisting of 1-2 moles of at least one of the amines substituted with N-alkyl, N-phenyl, N-alkylphenyl, N-phenylalkyl, N-methylbenzyl, N-hydroxyalkyl, N-hydroxypolyoxyalkyl and/or N-epoxyalkyl (the carbon number per one substituent being 1-8) having at least one hydroxyphenethyl group in the molecule and less than 1 mole of at least one of the amines substituted with N-alkyl, N-phenyl, N-alkylphenyl, N-phenylalkyl, N-methylbenzyl, N-hydroxyalkyl, N-hydroxypolyoxyalkyl and/or N-epoxyalkyl (the carbon number per one substituent being 1-8), or successively reacting the resultant product with 1-5 moles of at least one of the alkyl halides, hydroxyalkyl halides, hydroxypolyoxyalkyl halides, epoxyalkyl halides and alkyl esters of inorganic acids (the carbon number of the alkyl group being 1-8), or successively reacting the resultant product with 1-20 moles of at least one of formaldehyde, ethylene carbonate and alkylene oxide (the carbon number of the alkylene group being 2-8).

As examples of $\alpha,\omega$-alkylenediamines and $\alpha,\omega$-polyoxyalkylenediamines used as starting material in the said reaction process (i), there may be cited the following: hexylenediamine, octylenediamine, decylenediamine, undecylenediamine, hexadecylenediamine, octadecylenediamine, tetracosilenediamine, trioxyethylenediamine, tetraoxyethylenediamine, pentaoxyethylenediamine, hexaoxyethylenediamine, heptaoxyethylenediamine, octaoxyethylenediamine, trioxypropylenediamine, tetraoxypropylenediamine, pentaoxypropylenediamine, hexaoxypropylenediamine, heptaoxypropylenediamine, octaoxyethylenediamine and various types of N- and/or N'-substituents thereof. Examples of the monoamines used in the above-said reaction process (ii) are: N-methylamine, N-ethylamine, N-propylamine, N-butylamine, N-hexylamine, N-cyclohexylamine, N-octylamine, N-benzylamine, N-methylbenzylamine, aniline, N-hydroxyethylamine, N-hydroxypropylamine, N-hydroxybutylamine, N-hydroxyhexylamine, N-hydroxyoctylamine, N-hydroxyphenethylamine, N-hydroxyethoxyethylamine, N-hydroxydi(ethoxy)ethylamine, N-hydroxytri(ethoxy)ethylamine, N-hydroxypropoxypropylamine, N-glycidylamine and their styrene oxide addition products, and as examples of the alkylene dihalides and polyoxyalkylene dihalides, the following may be cited: 1,6-dichlorohexane, 1,6-dibromohexane, 1,8-dichlorooctane, 1,8-dibromooctane, 1,10-dichlorodecane, 1,10-dibromodecane, 1,12-dichlorodecane, 1,2-dibromododecane, 1,16-dichlorohexadecane, 1,16-dibromohexadecane, 1,18-dichlorooctadecane, 1,18-dibromooctadecane, 1,24-dichlorotetracosane, 1,24-dibromotetracosane, chloroethyloxyethyl=chloroethyl=ether, bromoethyloxyethyl=bromoethyl=ether, chloroethyldioxyethylene=chloroethyl=ether, bromoethyldioxyethylene=bromoethyl=ether,
chloroethyltrioxyethylene=chloroethyl=ether,
bromoethyltrioxyethylene=bromoethyl=ether, chloroethyltetraoxyethylene=chloroethyl=ether,
bromoethyltetraoxyethylene=bromoethyl=ether,
chloroethylpentaoxyethylene=chloroethyl=ether, bromoethylpentaoxyethylene=bromoethyl=ether,
chloroethylhexaoxyethylene=chloroethyl=ether,
bromoethylhexaoxyethylene=bromoethyl=ether, chloropropyloxypropyl=chloropropyl=ether,
bromopropyloxypropyl=bromopropyl=ether,
chloropropyldioxypropylene=chloropropylene=ether, bromopropyldioxypropylene=bromopropyl=ether,
chloropropyltrioxypropylene=chloropropyl=ether,
bromopropyltrioxypropylene=bromopropyl=ether, chloropropyltetraoxypropylene=chloropropyl=ether,
bromopropyltetraoxypropylene=bromopropyl=ether,
chloropropylpentaoxypropylene=chloropropyl=ether,
bromopropylpentaoxypropylene=bromopropyl=ether,
chloropropylhexaoxypropylene=chloropropyl=ether and
bromopropylhexaoxypropylene=bromopropyl=ether. As examples of the alkyl halides, hydroxyalkyl halides, hydroxypolyoxyalkyl halides and epoxyalkyl halides, there may be cited methyl chloride, methyl bromide, benzyl chloride, methylbenzyl chloride, ethylene chlorohydrin, ethylene bromohydrin, monochloroethoxy ethyl alcohol, monobromoethoxy ethyl alcohol, monochloroethoxyethyl=hydroxyethyl=ether, monobromoethoxyethyl=hydroxyethyl=ether, monochloroethoxyethyl=hydroxyethoxyethyl=ether, monobromoethoxyethyl=hydroxyethoxyethyl=ether, epichlorohydrin and epibromohydrin. The examples of alkylene oxide include, beside styrene oxide, the following: ethylene oxide, propylene oxide, butylene oxide, hexene oxide and octene oxide. The organic and inorganic acids used as active hydrogen donor in exiting a quaternarization reaction by an alkylene oxide in the cationic surface active agent preparation process of this invention are not subject to any specific restrictions, but the following are recommended for their easy availability: acetic acid, propionic acid, butyric acid, oxalic acid, hydrochloric acid, sulfuric acid, sulfurous acid, nitric acid, phosphoric acid, phosphorous acid, hypophosphorous acid, perchloric acid, hexafluorosilicic acid, paratoluenesulfonic acid and the like.

The cationic surface active agent preparing process according to this invention is now described in a more concrete way. The reaction between an $\alpha,\omega$-alkylenediamine or $\alpha,\omega$-polyoxyalkylenediamine and styrene oxide is carried out at a temperature of 100° to 250° C., preferably 150° to 200° C., under a pressure of from atmospheric pressure to 10 kg/cm$^2$, preferably 2.5–5 kg/cm$^2$. Although the reaction can proceed with no catalyst, it is free to add a non-polar or polar solvent as the reaction solvent. The attack reaction of an alkyl halide, hydroxyalkyl halide, hydroxypolyoxyalkyl halide, epoxyalkyl halide or an alkyl ester of an inorganic acid against the nitrogen atoms may be accomplished at a temperature of 30°–200° C., preferably 50°–150° C., under a pressure of from atmosphere pressure to 10 kg/cm$^2$, preferably 2.5–5 kg/cm$^2$. Use of a catalyst is not essential for this attack reaction, too, but addition of a solvent is effective in accelerating the reaction. The nitrogen atom attack reaction by an organic or inorganic acid can proceed under atmospheric pressure at a temperature of from normal temperature to 100° C., preferably 40°–80° C., but in this case, too, addition of a solvent proves helpful in promoting the reaction.

The addition reaction of formalin, ethylene carbonate or alkylene oxide to active hydrogen can progress at a temperature of 50°–250° C., preferably 80°–200° C., under a pressure of from atmospheric pressure to 15 kg/cm$^2$, preferably 2.5–5 kg/cm$^2$. In this case, the reaction is further promoted by use of an acid or an alkaline catalyst and addition of a reaction solvent.

On the other hand, the reaction between a monoamine and an alkylene dihalide or polyoxyalkylene dihalide can be accomplished at a temperature of 50°–250° C., preferably 100°–200° C., under a pressure of from atmospheric pressure to 10 kg/cm$^2$, preferably 3–7 kg/cm$^2$. Although no catalyst is required for this reaction, addition of a reaction solvent conduces to faster advancement of the reaction.

The fact that the cationic surface active agents of this invention can be prepared advantageously can be ascertained from observing the decrease of the total amine value and by confirming the absorption band of skeletal vibration of quaternary ammonium in the IR spectrum of the product.

The present inventors have further reached a finding that the cationic surface active agents prepared according to this invention can effectively act as a micellar catalyst or phase transfer catalyst, particularly in a system using an aqueous solution of an alkali metal hydroxide or an alkali earth metal hydroxide, to greatly contribute to promotion of rationalization of the process. Among the practical industrial processes using an aqueous solution of an alkali metal hydroxide or an alkali earth metal hydroxide are, for example, a process in which the fiber molecules are partly hydrolyzed with an alkali, like in georgette working or mercerization of polyester fibers, a process in which 3,4-dichlorobutene-1, which is a butadiene derivative, is dehydrochlorinated by an alkali treatment to convert it into 2-chlorobutadiene, a process in which 1,1,2-trichloroethane or 1,2-dichloroethane is dehydrochlorinated by an alkali treatment to convert it into vinylidene chloride or vinyl chloride, a process in which pulp is digested with an alkali to get rid of lignin, and many other important chemical and physical change processes. The cationic surface active agents of this invention have the properties that they are not biased either to the aqueous phase or to the non-aqueous phase and that they tend to gather round the interface, so that they display a catalytic function with small loadings in said processes and are also minimized in release into waste water after use. Thus, in practical use, the surface active agents of this invention can work as a lasting catalyst in said processes while arresting increase of organic carbon rate in waste water to conduce to environmental protection. Shown below are the embodiments of the invention.

EXAMPLE 1

186.3 g (1 mol) of undecylenediamine was fed into a five necked flask equipped with a stirrer, a thermometer, a gas inlet tube, a dropping funnel and an adaptor for connecting a condenser, and after heating said amine to 170° C., 240.2 g (2 mol) of styrene oxide was added dropwise thereto by spending approximately 2 hours, the mixture being allowed to react for one hour under the conditions of 170°-180° C. and atmospheric pressure to 2 kg/cm$^2$ and further aged until the epoxy oxygen content became less than 0.1%. After lowering the internal temperature to 125° C., 44.1 g (1 mol) of ethylene oxide was introduced under the conditions of 125°-135° C. and atmospheric pressure to 4 kg/cm$^2$ by spending approximately one hour and the mixture was further aged for one hour till the internal pressure returned to atmospheric pressure, resultantly obtaining an intermediate product N-(2-hydroxyethyl)-N,N'-di(2-hydroxyphenethyl)undecylenediamine (FIG. 1). Then, 571.6 g of ethylene glycol was added, and after diluting the mixture, 101 g (2 mol) of methyl chloride was introduced under the conditions of 90°-95° C. and atmospheric pressure-4 kg/cm$^2$ by taking approximately 5 hours, and the mixture was further aged for one hour until the internal pressure returned to the atmospheric pressure, thereby synthesizing the objective product of a hydrochloric acid neutralized substance of (methyl=2-hydroxyphenethyl)aminoundecyl=methyl=2-hydroxyethyl=2-hydroxystyryl=ammonium=chloride (FIG. 2).

Amine value of the product: 0.12 (theoretical: 0).

Confirmation of absorption band of quaternary nitrogen by IR spectral analysis (FIG. 2): 1160 cm$^{-1}$.

EXAMPLE 2

186.3 g (1 mol) of undecylenediamine and 240.2 g (2 mole) of styrene oxide were fed into the same reaction apparatus as used in Example 1 and reacted under the conditions of 180°-200° C. and atmospheric pressure-5 kg/cm$^2$ for 2 hours. Then the internal temperature was lowered to 140° C. and 88.2 g (1 mol) of ethylene oxide was introduced by using a time period of 2 hours, followed by aging of the mixture for additional one hour under the conditions of 140°-145° C. and 3-4 kg/cm$^2$. After further adding 615.7 g of dioxane, 101 g (2 mol) of methyl chloride was introduced under the conditions of 90°-95° C. and atmospheric pressure-4 kg/cm$^2$ by spending 5 hours to effect cationization, thereby synthesizing the objective 1,11-di(methyl=2-hydroxyethyl=2-hydroxyphenethyl=ammonium)undecane=dichloride.

Amine value of the product: 1.10 (theoretical: 0).

IR spectrum absorption band of quaternary nitrogen: 1160 cm$^{-1}$.

EXAMPLE 3

By following the pattern of Example 1, 240.2 g (2 mol) of styrene oxide and 44.1 g (1 mol) of ethylene oxide were added to 186.3 g (1 mol) of undecylenediamine, and the mixture was diluted by adding 723.8 g of butyl alcohol. Then, 253.2 g (2 mol) of benzyl chloride was supplied to the mixture to effect cationization under the conditions of atmospheric pressure and 125°-130° C. by spending approximately 15 hours to thereby synthesize the objective (benzyl=2-hydroxyphenethyl)aminoundecyl=benzyl=2-hydroxyethyl=2-hydroxyphenethyl=ammonium=chloride hydrochloride.

Amine value of the product: 0.55 (theoretical: 0).

IR spectrum absorption band of quaternary nitrogen: 1165 cm$^{-1}$.

EXAMPLE 4

240.2 g (2 mol) of styrene oxide and 88.2 g (1 mol) of ethylene oxide were added to 186.3 g (1 mol) of undecylenediamine and treated in the same way as Example 2, and the mixture was diluted by adding 767.9 g of butyl alcohol. Then 253.2 g (2 mole) of benzyl chloride was introduced to effect cationization under the conditions of 125°-130° C. and atmospheric pressure by spending approximately 20 hours to synthesize objective 1,11-di(benzyl=2-hydroxyethyl=2-hydroxyphenethyl=ammonium)undecane=dichloride.

Amine value of the product: 0.67 (theoretical: 0).

IR spectrum absorption band of quaternary nitrogen: 1165 cm$^{-1}$.

EXAMPLE 5

452.9 g (1 mol) of N,N'-trioctylhexamethylenediamine was fed into a reaction apparatus same as used in Example 1, and after adding dropwise thereto 120.1 g (1 mol) of styrene oxide, the mixture was reacted for 4 hours under the conditions of 180°-200° C. and atmospheric pressure-5 kg/cm$^2$. Then 257.1 g (1 mol) of monobromoethoxyethyl=hydroxyethoxyethyl=ether was fed to effect cationization under the conditions of 140°-150° C. and 4-5 kg/cm$^2$ by spending approximately 20 hours to synthesize (hexyl=2-hydroxyphenethyl)aminohexyl=dihexyl=hydroxyethyldioxyethyleneoxyethyl=ammonium=bromide.

Amine value of the product: 220.3 (theoretical: 218.2).

IR spectrum absorption band of quaternary nitrogen: 1162 cm$^{-1}$.

EXAMPLE 6

378.6 g (1 mol) of N-dimethyl-N'-methylbenzyloctaoxyethylenediamine and 120.1 g (1 mol) of styrene oxide were supplied into a reaction apparatus same as used in Example 1 and reacted under the conditions of 190°-200° C. and atmospheric pressure-5 kg/cm$^2$ for four hours. After further adding 625 g of isopropyl alcohol, 126.3 g (1 mol) of dimethylsulfuric acid was added dropwise under atmospheric pressure at 70°-75°

C. for a period of one hour, and the mixture was further aged under the same conditions for one hour to effect cationization, thereby synthesizing (methylbenzyl≡2-hydroxyphenethyl)aminoethylhexaoxyethyleneoxyethyl≡trimethyl≡ammonium≡methylsulfate.

Amine value of the product: 90.0 (theoretical: 89.8).

IR spectrum absorption band of quaternary nitrogen: 1162 cm$^{-1}$.

EXAMPLE 7

692.9 g (1 mol) of N-diphenyl-N'-hydroxyethyloctaoxypropylenediamine and 120.1 g (1 mol) of styrene oxide were fed into the same reaction apparatus as used in Example 1 and reacted under the conditions of 140°–150° C. and atmospheric pressure-2 kg/cm$^2$ for 2 hours. Then, after further adding thereto 905.5 g (1 mol) of ethylene glycol, 92.5 g (1 mol) of epichlorohydrin was supplied to effectuate cationization under the conditions of atmospheric pressure and 120°–125° C., taking a time of 6 hours, to synthesize diphenylaminopropylhexaoxypropyleneoxypropyl≡2-hydroxyethyl≡2-hydroxyphenethyl≡glycidyl≡ammonium≡chloride.

Amine value of the product: 64.1 (theoretical: 62.0).

IR spectrum absorption band of quaternary nitrogen: 1162 cm$^{-1}$.

EXAMPLE 8

456.8 g (1 mol) of N,N'-di(2-hydroxyethyl)tetracosylenediamine and 120.1 g (1 mol) of styrene oxide were supplied into a reaction apparatus same as used in Example 1, and they were reacted under the conditions of 180°–190° C. and atmospheric pressure-3 kg/cm$^2$ for 3 hours. This was followed by further addition of 88.1 g (1 mol) of ethylene carbonate and reaction of the mixture under the conditions of 120°–130° C. and atmospheric pressure-3 kg/cm$^2$ for 2 hours, and after diluting the reaction product by adding 1,153 g of ethylene glycol, 208.6 g (equivalent to 2 mol) of a 35% hydrochloric acid solution was added dropwise under atmospheric pressure at 50°–60° C. for a period of 2 hours, followed by further addition of 162.3 g (equivalent to 2 mol) of a 37% formalin solution to effect quaternarization under atmospheric pressure at 70°–80° C. by taking 5 hours to synthesize 1-(hydroxymethyl≡2-hydroxyethyl≡2-hydroxyphenethyl)ammonium-24-{hydroxymethyl≡di(2-hydroxyethyl)}ammoniumtetracosane≡dichloride.

Amine value of the product: 0 (theoretical: 0).

IR spectrum absorption band of quaternary nitrogen: 1160 cm$^{-1}$.

EXAMPLE 9

284.5 g (1 mol) of octadecylenediamine and 120.1 g (1 mol) of styrene oxide were fed into a reaction apparatus similar to that of Example 1 and reacted under the conditions of 180°–190° C. and atmospheric pressure-3 kg/cm$^2$ for 3 hours. Then 132 g (2 mol) of hypophorous acid was supplied to accomplish a neutralization reaction at 70°–80° C. for one hour, and after further adding 0.5 g of boron trifluoride etherate, 882 g (20 mol) of ethylene oxide was introduced under the conditions of 100°–120° C. and atmospheric pressure-4 kg/cm$^2$ by taking a time of 6 hours, followed by further aging for one hour under the same conditions to thereby synthesize 1-{di(hydroxypolyethyleneoxyethyl)≡2-hydroxyphenethyl}ammonium-18-{tri(hydroxypolyethyleneoxyethyl)}ammoniumoctadecane≡dihypophosphite.

Amine value of the product: 1.60 (theoretical: 0).

IR spectrum absorption band of quaternary nitrogen: 1160 cm$^{-1}$.

EXAMPLE 10

186.3 g (1 mol) of undecylenediamine was fed into a reaction apparatus similar to Example 1, followed by introduction of 120.1 g (1 mol) of styrene oxide under the conditions of 170°–180° C. and atmospheric pressure-2 kg/cm$^2$ for a period of three hours and additional one-hour aging of the mixture under the same conditions. After further adding 0.6 g of sodium carbonate, 697.2 g (12 mol) of propylene oxide was introduced under the conditions of 100°–130° C. and atmospheric pressure-5 kg/cm$^2$ for a period of 6 hours and the mixture was aged under the same conditions for one hour. After diluting the reaction mixture by adding 1,253.6 g of methyl cellosolve, 250 g (2 moles) of ethylenebromohydrin was fed to effect cationization under atmospheric pressure at 120°–130° C. by taking 20 hours to thereby synthesiz 1-(hydroxypolypropyleneoxypropyl≡2-hydroxyethyl≡2-hydroxyphenethyl)ammonium-11-{di(hydroxypolypropyleneoxypropyl)≡2-hydroxyethyl}ammoniumundecane≡dibromide.

Amine value of the product: 1.85 (theoretical: 0).

IR spectrum absorption band of quaternary nitrogen: 1160 cm$^{-1}$.

EXAMPLE 11

344.5 g (1 mol) of N,N'-dibenzyltrioxyethylenediamine was fed into the reaction apparatus of Example 1 and reacted with 120.1 g (1 mol) of styrene oxide under the conditions of 180°–190° C. and atmospheric pressure-5 kg/cm$^2$ for a period of 3 hours. After diluting the reaction mixture by adding 897.2 g of dioxane, 344.4 g (2 mol) of toluenesulfonic acid was added to effectuate a neutralization reaction under atmospheric pressure at 70°–80° C. for one hour, followed by introduction of 88.2 g (2 mol) of ethylene oxide under the same conditions by taking 10 hours and additional one-hour aging to effect quaternarization, thereby synthesizing a toluenesulfonic acid-neutralized substance of (benzyl≡2-hydroxyphenethyl)aminoethoxyethoxyethyl≡benzyl≡di(2-hydroxyethyl)≡ammonium≡toluenesulfonate.

Amine value of the product: 0.90 (theoretical: 0).

IR spectrum absorption band of quaternary nitrogen: 1165 cm$^{-1}$.

EXAMPLE 12

580.7 g (1 mol) of N-diphenyl-N'-hydroxyethyloctaoxyethylenediamine and 120.1 g (1 mol) of styrene oxide were fed into the reaction apparatus of Example 1 and reacted under the condition of 190°–200° C. and atmospheric pressure-5 kg/cm$^2$ for a period of 4 hours. After diluting the reaction mixture by adding 500 g of butyl alcohol, 203.2 g (2 mol) of 62%-silver nitrate aqueous solution was added dropwise by taking 2 hours at 50°–60° C. under an atmospheric pressure, followed by introduction of 58.1 g (1 mol) of propylene oxide under the condition of 80°–90° C. by taking 2 hours, and addition one-hour aging to effect quaternarization under the same conditions, thereby synthesizing a nitric acid-neutralized substance of diphenylaminoethylhexaoxyethyleneoxyethyl≡2-hydroxyethyl≡2-hydroxypropyl≡2-hydroxyphenethyl≡ammonium≡nitrate.

Amine value of the product: 0 (theoretical: 0).

IR spectrum absorption band of quaternary nitrogen: 1163 cm$^{-1}$.

EXAMPLE 13

116.2 g (1 mol) of hexamethylenediamine was fed into a reaction apparatus same as used in Example 1, then 480.4 g (4 mol) of styrene oxide was added dropwise thereto under atmospheric pressure at 170°–180° C. by spending approximately 3 hours and the mixture was reacted for 2 hours at the same temperature under a pressure within the range of atmospheric pressure to 5 kg/cm$^2$. After diluting the reaction mixture by adding 786.5 g of ethyl alcohol, 189.9 g (2 mol) of methyl bromide was introduced at 70°–80° C. under atmospheric pressure to 2 kg/cm$^2$ by taking 3 hours and the mixture was further aged under the same conditions for one hour to effect cationization, thereby synthesizing 1,6-di{methyl=di(2-hydroxyphenethyl)=ammonium}hexane=dibromide.

Amine value of the product: 1.86 (theoretical: 0).

IR spectrum absorption band of quaternary nitrogen: 1165 cm$^{-1}$.

EXAMPLE 14

390.5 g (2 mol) of methyl=2-hydroxyethyl=2-hydroxystyryl=amine and 239.2 g (1 mol) of 1,12-dichlorododecane were fed into a reaction apparatus same as used in Example 1, and by further adding 630 g of butyl alcohol, the mixture was cationized under the conditions of 140°–150° C. and 3–5 kg/cm$^2$ by spending 30 hours to synthesize 1,12-di(methyl=2-hydroxyethyl=2-hydroxyphenethyl=ammonium)dodecane=dichloride.

Amine value of the product: 2.68 (theoretical: 0).

IR spectrum absorption band of quaternary nitrogen: 1160 cm$^{-1}$.

EXAMPLE 15

542.7 g (2 mol) of benzyl=2-hydroxyethyl=2-hydroxyphenethyl=amine and 328.1 g (1 mol) of 1,12-dibromododecane were supplied into the same apparatus as used in Example 1, followed by addition of 870 g of ethylene glycol and 40-hour cationization under the conditions of 150°–160° C. and 5–6 kg/cm$^2$ to synthesize 1,12-di(benzyl=2-hydroxyethyl=2-hydroxyphenethyl=ammonium)dodecane=dibromide.

Amine value of the product: 2.91 (theoretical: 0).

IR spectrum absorption band of quaternary nitrogen: 1160 cm$^{-1}$.

EXAMPLE 16

542.7 g (2 mol) of benzyl=2-hydroxyethyl=2-hydroxyphenethyl=amine and 319.2 g (1 mol) of chloroethyltetraoxyethylene=chloroethyl=ether were fed into a reaction apparatus of the type used in Example 1, and after adding 862 g of di(methoxyethyl)=ether, the reaction mixture was cationized under the conditions of 150°–155° C. and atmospheric pressure-3 kg/cm$^2$ for a period of 20 hours to synthesize 1,17-di(benzyl=2-hydroxyethyl=2-hydroxyphenethyl=ammonium)hexaoxyethylene=dichloride.

Amine value of the product: 0.42 (theoretical: 0).

IR spectrum absorption band of quaternary nitrogen: 1162 cm$^{-1}$.

EXAMPLE 17

450.6 g (2 mol) of di(2-hydroxyethyl)=2-hydroxyphenethyl=amine and 319.2 g (1 mol) of chloroethyltetraoxyethylene=chloroethyl=ether were fed into a reaction apparatus same as used in Example 1, followed by 20-hours cationization under the conditions of 160°–170° C. and atmospheric pressure-3 kg/cm$^2$ to synthesize 1,17-di{di(2-hydroxyethyl)=2-hydroxyphenethyl=ammonium}hexaoxyethylene=dichloride.

Amine value of the product: 0.13 (theoretical: 0).

IR spectrum absorption band of quaternary nitrogen: 1162 cm$^{-1}$.

EXAMPLE 18

454.6 g (2 mol) of benzyl=2-hydroxyphenethyl=amine and 328.1 g (1 mol) of 1,12-dibromododecane were fed into a reaction apparatus similar to that used in Example 1, and after further adding 826.8 g of ethylene glycol, cationization was accomplished under the conditions of 160°–170° C. and 4–6 kg/cm$^2$ by using 30 hours. Thereafter, 44.1 g (1 mol) of ethylene oxide was introduced under the conditions of 90°–100° C. and atmospheric pressure to 4 kg/cm$^2$ by spending 1 hour, followed by one-hour aging to effect quaternarization to thereby synthesize a hydrobromic acid-neutralized substance of (benzyl=2-hydroxyphenethyl)aminododecyl=benzyl=2-hydroxyethyl=2-hydroxyphenethyl=ammonium=bromide.

Amine value of the product: 2.05 (theoretical: 0).

IR spectrum absorption band of quaternary nitrogen: 1165 cm$^{-1}$.

EXAMPLE 19

362.5 g (2 mol) of 2-hydroxyethyl-2-hydroxyphenethyl=amine and 319.2 g (1 mol) of chloroethyltetraoxyethylene=chloroethyl=ether were fed into the reaction apparatus used in Example 1 and the mixture was cationized under the conditions of 160°–170° C. and 3–5 kg/cm$^2$ by requiring one hour. Thereafter, 44.1 g (1 mol) of ethylene oxide was introduced under the conditions of 90°–100° C. and 2–4 kg/cm$^2$ for a period of one hour, followed by one-hour aging at the same temperature to perform quaternarization, thereby synthesizing a hydrochloric acid-neutralized product of (2-hydroxyethyl=2-hydroxyphenethyl)aminoethyltetraoxyethyleneoxyethyl=di(2-hydroxyethyl)=2-hydroxyphenethyl=ammonium=chloride.

Amine value of the product: 0.37 (theoretical: 0).

IR spectrum absorption band of quaternary nitrogen: 1161 cm$^{-1}$.

EXAMPLE 20

426.6 g (2 mol) of phenyl=2-hydroxystyryl=amine and 155.0 g (1 mol) of dichlorohexane were fed into a reaction apparatus such as used in Example 1, and after adding 630 g of di(methoxyethyl)=ether, the mixture was reacted under the conditions of 140°–145° C. and 5–6 kg/cm$^2$ for 40 hours, which was followed by further addition of 40 g (1 mol) of sodium hydroxide and 3-hour-period introduction of 50.5 g (1 mol) of methyl chloride at 100°–110° C. under atmospheric pressure to 5 kg/cm$^2$ to effectuate cationization, thereby synthesizing a hydrochloric acid neutralization product of (phenyl=2=hydroxyphenethyl)aminohexyl=methyl=phenyl=2-hydroxyphenethyl=ammonium=chloride.

Amine value of the product: 2.23 (theoretical: 0).

IR spectrum absorption band of quaternary nitrogen: 1165 cm$^{-1}$.

EXAMPLE 21

390.5 g (2 mol) of methyl=hydroxyethoxyethyl=2-hydroxyphenethylamine and 496.5 g (1 mol) of 1,24-dibromotetracosane were fed into a reaction apparatus similar to that used in Example 1, and after adding 887 g of ethylene glycol, cationization was performed under the conditions of 160°–170° C. and 3–6 kg/cm² by spending 30 hours to synthesize 1,24-di(methyl═hydroxyethoxy-ethyl═2-hydroxyphenethylammonium)-tetracosane.

Amine value of the product: 2.89 (theoretical: 0).

IR spectrum absorption band of quaternary nitrogen: 1160 cm⁻¹.

EXAMPLE 22

301.3 g (1 mol) of 2-hydroxyethyl═di(2-hydrophenethyl)amine, 149.2 g (1 mol) of dimethyl═methylbenzylamine, 173.0 g (1 mol) of chloroethoxyethyl═chloroethyl═ether and 623.6 g of ethylene glycol were fed into the reaction apparatus of Example 1 and cationization was conducted under the conditions of 150°–160° C. and atmospheric pressure to 5 kg/cm² by using a time of 20 hours to synthesize 1-{2-hydroxyethyl═di(2-hydroxyphenethyl)ammonium}-8-(dimethyl═methylbenzylammonium)trioxyethylene═dichloride.

Amine value of the product: 1.11 (theoretical: 0).

IR spectrum absorption band of quaternary nitrogen: 1164 cm⁻¹.

EXAMPLE 23

369.6 g (1 mol) of octyl═di(2-hydroxyphenethyl)amine, 129.3 g (1 mol) of octylamine and 755.3 g (1 mol) of bromopropylhexaoxypropylene═bromopropyl═ether were fed into a reaction apparatus same as employed in Example 1 and reacted under the conditions of 140°–150° C. and 3–5 kg/cm² for 20 hours, followed by further addition of 256.4 g (2 mol) of octene oxide and 10-hour-period quaternarization under the conditions of 150°–160° C. and 5–6 kg/cm² to synthesize 1-{octyl═di(2-hydroxyphenethyl)ammonium}-23{octyl═di(2-hydroxyoctyl)ammonium}octaoxypropylene═dibromide.

Amine value of the product: 1.20 (theoretical: 0).

IR spectrum absorption band of quaternary nitrogen: 1170 cm⁻¹.

EXAMPLE 24

386.6 g (2 mol) of butyl═2-hydroxyphenethyl═amine and 408.1 g (1 mol) of bromoethyltetraoxyethylene═bromoethyl═ether were fed into a reaction apparatus identical with that used in Example 1, and after adding thereto 921 g of di(methoxyethyl)═ether, the mixture was reacted under the conditions of 140°–150° C. and 3–5 kg/cm² for 30 hours, followed by further addition of 112.2 g (2 mol) of potassium hydroxide, dropwise addition of 126.3 g (1 mol) of dimethylsulfuric acid under atmospheric pressure at 80°–85° C. for a period of one hour and one-hour cationization under the same conditions to thereby synthesize (butyl═2-hydroxyphenethyl)aminoethyltetraoxyethyleneoxyethyl═methyl═butyl═2-hydroxystyryl═ammonium═methylsulfate.

Amine value of the product: 67.3 (theoretical: 66.8).

IR spectrum absorption band of quaternary nitrogen: 1160 cm⁻¹.

EXAMPLE 25

277.4 g (1 mol) of cyclohexyl═2-hydroxypropyl═2-hydroxyphenethyl═amine, 105.1 g (1 mol) of di(2-hydroxyethyl)amine, 328.1 g (1 mol) of 1,12-dibromododecane and 1,210 g of di(methoxyethyl)═ether were fed into a reaction apparatus of the same type as employed in Example 1, and cationization was performed under the conditions of 140°–150° C. and 3–5 kg/cm² by spending 30 hours. Then 81.2 g (equivalent to 1 mol) of a 37% formalin solution was added to accomplish quaternarization under atmospheric pressure at 70°–80° C. by requiring 5 hours to thereby synthesize 1-(cyclohexyl═2-hydroxypropyl═2-hydroxyphenethyl)ammonium-12{hydroxymethyl═di(2-hydroxyethyl)}ammoniumdodecane═dibromide.

Amine value of the product: 1.12 (theoretical: 0).

IR spectrum absorption band of quaternary nitrogen: 1160 cm⁻¹.

EXAMPLE 26

482.7 g (2 mol) of methylbenzyl═2-hydroxyphenethyl═amine and 408.1 g (1 mol) of bromoethyltetraoxyethylene═bromoethyl═ether were fed into a reaction apparatus similar to that of Example 1 and reacted under the conditions of 150°–160° C. and 3–6 kg/cm² for 25 hours. Then 80 g (2 mol) of sodium hydroxide was added to the reaction mixture, followed by dropwise addition of 185 g (2 mol) of epichlorohydrin under atmospheric pressure at 90°–95° C. for a period of 3 hours and one-hour-period quaternarization under the same conditions to synthesize 1,17-di(methylbenzyl═2-hydroxyphenethyl═gylcidyl)ammonium═hexaoxyethylene═dibromide.

Amine value of the product: 0.41 (theoretical: 0).

IR spectrum absorption band of quaternary nitrogen: 1165 cm⁻¹.

EXAMPLE 27

522.8 g (2 mol) of 2-ethylhexyl═2-hydroxyphenethyl═amine and 332.1 g (1 mol) of bromoethoxyhexyl═bromoethyl═ether were fed into a reaction apparatus of the same type as used in Example 1 and reacted under the conditions of 150°–160° C. and 3–5 kg/cm² for 30 hours. After additionally feeding 88.1 g (1 mol) of ethylene carbonate, the mixture was reacted under the conditions of 120°–130° C. and atmospheric pressure-3 kg/cm² for 2 hours and quaternarized to synthesize a hydrobromic acid neutralization product of (2-ethylhexyl═2-hydroxyphenethyl)aminoethoxyhexyl═2-ethylhexyl═2-hydroxyethyl═2-hydroxyphenethyl-═ammonium═bromide.

Amine value of the product: 0.88 (theoretical: 0).

IR spectrum absorption band of quaternary nitrogen: 1160 cm⁻¹.

EXAMPLE 28

Described hereinbelow is the effect of the cationic surface active agents of this invention in accelerating the hydrolytic reaction of polyester in alkaline aqueous solutions. Table 1 shows the results of measurement of percent loss in weight of polyester taffeta when the cationic surface active agents synthesized in Examples 1–27 were used as hydrolysis accelerator. The test method was as follows.

(1) Test conditions

Test fabric: polyester (polyethylene terephthalate) taffeta

Bath ratio: 1:100 (The treating bath was prepared by adding a test quantity of each cationic surface active agent in a 1% NaOH solution)

Treating temperature: 95° C. (constant)

Treating solution stirring speed: 30 r.p.m.

(2) Test apparatus

Color Master HD-12 manufactured by Tujii Senki Co., Ltd.

(3) Calculation of percent loss of weight
The percent loss of weight was calculated from the following formula:

$$\text{loss}(\%) = \frac{[\text{initial weight of fabric}] - [\text{weight after treatment}]}{[\text{initial weight of fabric}]} \times 100\ (\%)$$

TABLE 1

Percent loss of weight of polyester taffeta from hydrolysis in alkaline solution

| Sample added | Amount (g) added per 1 kg of 1% NaOH solution | Percent loss of weight after 30-minute treatment at 95° C. | Percent loss of weight after 60-minute treatment at 95° C. |
|---|---|---|---|
| Blank test (no additive) | — | 3.7% | 5.2% |
| Cationic surface active agent synthesized in Example 1 | 0.20 | 22.2 | 32.7 |
| Cationic surface active agent synthesized in Example 1 | 0.50 | 30.1 | 47.1 |
| Cationic surface active agent synthesized in Example 2 | 0.25 | 20.3 | 30.3 |
| Cationic surface active agent synthesized in Example 2 | 0.75 | 30.0 | 45.2 |
| Cationic surface active agent synthesized in Example 3 | 0.30 | 22.3 | 33.1 |
| Cationic surface active agent synthesized in Example 3 | 0.60 | 31.2 | 47.0 |
| Cationic surface active agent synthesized in Example 4 | 0.35 | 20.0 | 29.3 |
| Cationic surface active agent synthesized in Example 4 | 1.05 | 28.2 | 40.5 |
| Cationic surface active agent synthesized in Example 5 | 0.50 | 17.3 | 30.9 |
| Cationic surface active agent synthesized in Example 5 | 1.50 | 29.9 | 39.0 |
| Cationic surface active agent synthesized in Example 6 | 0.45 | 21.1 | 30.1 |
| Cationic surface active agent synthesized in Example 6 | 0.90 | 31.1 | 43.2 |
| Cationic surface active agent synthesized in Example 7 | 1.00 | 16.1 | 22.3 |
| Cationic surface active agent synthesized in Example 7 | 1.50 | 20.1 | 32.7 |
| Cationic surface active agent synthesized in Example 8 | 1.50 | 15.3 | 21.2 |
| Cationic surface active agent synthesized in Example 8 | 2.00 | 19.8 | 30.1 |
| Cationic surface active agent synthesized in Example 9 | 0.80 | 22.3 | 33.1 |
| Cationic surface active agent synthesized in Example 9 | 1.60 | 27.7 | 48.6 |
| Cationic surface active agent synthesized in Example 10 | 0.50 | 18.9 | 28.8 |
| Cationic surface active agent synthesized in Example 10 | 1.00 | 23.9 | 36.1 |
| Cationic surface active agent synthesized in Example 11 | 1.00 | 16.7 | 29.0 |
| Cationic surface active agent synthesized in Example 11 | 2.00 | 22.1 | 31.1 |
| Cationic surface active agent synthesized in Example 12 | 1.00 | 18.6 | 30.2 |
| Cationic surface active agent synthesized in Example 12 | 2.00 | 23.3 | 35.5 |
| Cationic surface active agent synthesized in Example 13 | 0.20 | 22.0 | 32.0 |
| Cationic surface active agent synthesized in Example 13 | 0.50 | 29.8 | 47.0 |
| Cationic surface active agent synthesized in Example 14 | 0.25 | 20.3 | 30.2 |
| Cationic surface active agent synthesized in Example 14 | 0.75 | 31.5 | 46.0 |
| Cationic surface active agent synthesized in Example 15 | 0.30 | 21.9 | 32.7 |
| Cationic surface active agent synthesized in Example 15 | 0.60 | 33.1 | 47.0 |
| Cationic surface active agent synthesized in Example 16 | 0.20 | 24.6 | 35.1 |
| Cationic surface active agent synthesized in Example 16 | 0.40 | 29.0 | 44.4 |
| Cationic surface active agent synthesized in Example 17 | 0.20 | 25.6 | 36.8 |
| Cationic surface active agent | 0.40 | 32.0 | 47.0 |

TABLE 1-continued

Percent loss of weight of polyester taffeta from hydrolysis in alkaline solution

| Sample added | Amount (g) added per 1 kg of 1% NaOH solution | Percent loss of weight after 30-minute treatment at 95° C. | Percent loss of weight after 60-minute treatment at 95° C. |
|---|---|---|---|
| Cationic surface active agent synthesized in Example 17 | 0.20 | 20.3 | 32.1 |
| Cationic surface active agent synthesized in Example 18 | 0.40 | 29.3 | 44.3 |
| Cationic surface active agent synthesized in Example 18 | 0.20 | 21.1 | 32.4 |
| Cationic surface active agent synthesized in Example 19 | 0.40 | 31.3 | 46.0 |
| Cationic surface active agent synthesized in Example 19 | 0.90 | 20.0 | 30.1 |
| Cationic surface active agent synthesized in Example 20 | 1.80 | 28.8 | 39.1 |
| Cationic surface active agent synthesized in Example 20 | 1.00 | 18.2 | 29.0 |
| Cationic surface active agent synthesized in Example 21 | 2.00 | 23.0 | 33.3 |
| Cationic surface active agent synthesized in Example 21 | 0.15 | 18.9 | 30.3 |
| Cationic surface active agent synthesized in Example 22 | 0.30 | 20.0 | 37.3 |
| Cationic surface active agent synthesized in Example 22 | 0.30 | 17.2 | 29.0 |
| Cationic surface active agent synthesized in Example 23 | 0.60 | 24.3 | 33.3 |
| Cationic surface active agent synthesized in Example 23 | 0.10 | 16.2 | 29.8 |
| Cationic surface active agent synthesized in Example 24 | 0.30 | 24.1 | 40.0 |
| Cationic surface active agent synthesized in Example 24 | 0.20 | 20.0 | 30.8 |
| Cationic surface active agent synthesized in Example 25 | 0.50 | 28.7 | 44.9 |
| Cationic surface active agent synthesized in Example 25 | 0.20 | 18.9 | 28.9 |
| Cationic surface active agent synthesized in Example 26 | 0.50 | 27.7 | 40.3 |
| Cationic surface active agent synthesized in Example 26 | 0.30 | 18.0 | 28.0 |
| Cationic surface active agent synthesized in Example 27 | 0.60 | 26.2 | 39.9 |
| Dodecyltrimethylammonium:chloride* | 1.00 | 7.3 | 12.2 |
| Dodecyltrimethylammonium:chloride* | 2.00 | 8.2 | 14.8 |
| 1,11-di{methyl=di(2-hydroxyethyl)=ammonium}undecane=dichloride** | 1.00 | 4.2 | 12.0 |
| 1,11-di{methyl=di(2-hydroxyethyl)=ammonium}undecane=dichloride** | 2.00 | 6.8 | 13.3 |

Notes:
*Dodecyltrimethylammonium=chloride is a known cationic surface active agent used here as a comparative product.
**1,11-di{methyl=di(2-hydroxyethyl)=ammonium}undecane=dichloride is an N,N'—long-chain alkylene type cationic surface active agent having no hydroxyphenethyl group, used here as a comparative product.

EXAMPLE 29

Shown here is the effect of the cationic surface active agents of this invention in promoting the dehydrochlorination reaction of the organic chlorine compounds in an alkaline aqueous solution. The reaction for synthesizing 2-chlorobutadiene from 3,4-dichlorobutene-1 was used here. The test method was as follows.

(1) Testing conditions
Reaction molar ratio and proportions of the materials charged:

| (1) organic phase: | 3,4,-dichlorobutene-1 | 62.5 g (0.5 mol) |
|---|---|---|
| | Toluene | 94 g |
| (2) Aqueous phase: | Sodium hydroxide | 22 g (0.55 mol) |
| | Water | 78 g |

| (3) Reaction accelerator: | test quantity of each of the cationic surface active agents synthesized in Examples 1–27 |
|---|---|

Reaction temperature: 50° C. (constant)
Stirring rate: 1,200 r.p.m.
(2) Test apparatus
Four-necked flask equipped with a stirrer, a thermometer, a dropping funnel and a reflux condenser.
(3) Calculation of 2-chlorobutadiene formation rate
The reaction product was subjected to 80° C. constant-temperature gas chromatographic analysis by using a column with silicon DC-550 as carrier, and the 2-chlorobutadiene formation rate was calculated from the peak area ratio of 3,4-dichlorobutene-1 to 2-chlorobutadiene given on the chart.
The test results are shown in Table 2.

TABLE 2

2-Chlorobutadiene formation rate in toluene solution-sodium hydroxide solution system of 3,4-dichlorobutene

| Sample added | Amount (g) added per 62.5 g of 3,4-dichlorobutene-1 | 2-Chlorobutadiene formation rate after 30-minute treatment at 50° C. | 2-Chlorobutadiene formation rate after 60-minute treatment at 50° C. |
|---|---|---|---|
| Blank test (no additive) | — | 2.7% | 3.8% |
| Cationic surface active agent synthesized in Example 1 | 0.03 | 17.0 | 22.5 |
| Cationic surface active agent synthesized in Example 1 | 0.30 | 67.3 | 85.9 |
| Cationic surface active agent synthesized in Example 2 | 0.05 | 16.1 | 20.1 |
| Cationic surface active agent synthesized in Example 2 | 0.35 | 65.8 | 84.3 |
| Cationic surface active agent synthesized in Example 3 | 0.05 | 20.1 | 27.1 |
| Cationic surface active agent synthesized in Example 3 | 0.30 | 67.3 | 87.2 |
| Cationic surface active agent synthesized in Example 4 | 0.07 | 15.0 | 19.0 |
| Cationic surface active agent synthesized in Example 4 | 0.40 | 60.3 | 80.3 |
| Cationic surface active agent synthesized in Example 5 | 0.06 | 12.1 | 15.9 |
| Cationic surface active agent synthesized in Example 5 | 0.60 | 45.2 | 74.0 |
| Cationic surface active agent synthesized in Example 6 | 0.06 | 15.2 | 22.3 |
| Cationic surface active agent synthesized in Example 6 | 0.70 | 62.7 | 80.1 |
| Cationic surface active agent synthesized in Example 7 | 0.10 | 12.0 | 14.8 |
| Cationic surface active agent synthesized in Example 7 | 1.00 | 40.3 | 50.2 |
| Cationic surface active agent synthesized in Example 8 | 0.20 | 13.3 | 16.8 |
| Cationic surface active agent synthesized in Example 8 | 1.00 | 41.3 | 52.2 |
| Cationic surface active agent synthesized in Example 9 | 0.15 | 17.9 | 28.1 |
| Cationic surface active agent synthesized in Example 9 | 0.60 | 68.5 | 83.4 |
| Cationic surface active agent synthesized in Example 10 | 0.06 | 15.1 | 20.1 |
| Cationic surface active agent synthesized in Example 10 | 0.80 | 55.1 | 78.2 |
| Cationic surface active agent synthesized in Example 11 | 0.50 | 10.3 | 14.2 |
| Cationic surface active agent synthesized in Example 11 | 1.50 | 30.1 | 49.3 |
| Cationic surface active agent synthesized in Example 12 | 0.50 | 11.3 | 15.4 |
| Cationic surface active agent synthesized in Example 12 | 2.00 | 30.2 | 49.7 |
| Cationic surface active agent synthesized in Example 13 | 0.03 | 11.0 | 15.0 |
| Cationic surface active agent synthesized in Example 13 | 0.30 | 47.1 | 70.0 |
| Cationic surface active agent synthesized in Example 14 | 0.05 | 17.0 | 22.0 |
| Cationic surface active agent synthesized in Example 14 | 0.35 | 67.0 | 85.1 |
| Cationic surface active agent synthesized in Example 15 | 0.05 | 17.2 | 24.1 |
| Cationic surface active agent synthesized in Example 15 | 0.35 | 66.0 | 84.1 |
| Cationic surface active agent synthesized in Example 16 | 0.03 | 16.2 | 21.1 |
| Cationic surface active agent synthesized in Example 16 | 0.30 | 60.0 | 74.1 |
| Cationic surface active agent synthesized in Example 17 | 0.20 | 14.3 | 17.9 |
| Cationic surface active agent synthesized in Example 17 | 0.20 | 58.1 | 71.2 |
| Cationic surface active agent synthesized in Example 18 | 0.03 | 17.3 | 24.2 |

TABLE 2-continued

2-Chlorobutadiene formation rate in toluene solution-sodium hydroxide solution system of 3,4-dichlorobutene

| Sample added | Amount (g) added per 62.5 g of 3,4-dichloro-butene-1 | 2-Chlorobuta-diene formation rate after 30-minute treat-ment at 50° C. | 2-Chlorobuta-diene formation rate after 60-minute treat-ment at 50° C. |
| --- | --- | --- | --- |
| Cationic surface active agent synthesized in Example 18 | 0.30 | 66.1 | 84.0 |
| Cationic surface active agent synthesized in Example 19 | 0.03 | 14.9 | 18.0 |
| Cationic surface active agent synthesized in Example 19 | 0.25 | 60.0 | 72.9 |
| Cationic surface active agent synthesized in Example 20 | 0.05 | 12.3 | 18.2 |
| Cationic surface active agent synthesized in Example 20 | 1.50 | 60.0 | 70.1 |
| Cationic surface active agent synthesized in Example 21 | 0.50 | 10.3 | 14.0 |
| Cationic surface active agent synthesized in Example 21 | 2.00 | 29.3 | 47.8 |
| Cationic surface active agent synthesized in Example 22 | 0.10 | 10.1 | 12.1 |
| Cationic surface active agent synthesized in Example 22 | 0.40 | 23.1 | 45.0 |
| Cationic surface active agent synthesized in Example 23 | 0.05 | 12.3 | 17.1 |
| Cationic surface active agent synthesized in Example 23 | 0.40 | 40.3 | 69.0 |
| Cationic surface active agent synthesized in Example 24 | 0.01 | 9.0 | 12.0 |
| Cationic surface active agent synthesized in Example 24 | 1.00 | 36.1 | 60.3 |
| Cationic surface active agent synthesized in Example 25 | 0.03 | 15.8 | 19.9 |
| Cationic surface active agent synthesized in Example 25 | 0.30 | 60.1 | 70.8 |
| Cationic surface active agent synthesized in Example 26 | 0.03 | 15.0 | 19.0 |
| Cationic surface active agent synthesized in Example 26 | 0.30 | 55.3 | 70.0 |
| Cationic surface active agent synthesized in Example 27 | 0.05 | 15.0 | 19.6 |
| Cationic surface active agent synthesized in Example 27 | 0.50 | 59.9 | 76.1 |
| Dodecyltrimethylammonium=chloride | 0.10 | 3.8 | 12.0 |
| Dodecyltrimethylammonium=chloride | 1.00 | 20.0 | 38.2 |
| 1,11-di(methyl=di(2-hydroxyethyl)-ammonium)undecane=dichloride | 0.10 | 2.9 | 3.9 |
| 1,11-di(methyl=di(2-hydroxyethyl)-ammonium)undecane=dichloride | 1.00 | 9.2 | 12.0 |

EXAMPLE 30

Shown here is the reaction-promoting effect of the cationic surface active agents of this invention as seen in the reaction for synthesizing 2-chlorobutadiene from 3,4-dichlorobutene-1 as in the case of Example 29. A barium hydroxide suspension was used as aqueous phase. The test method is as follows.

(1) Test conditions
Reaction molar ratio and proportions of the materials charged:

| (1) Organic phase: | 3,4-dichlorobutene | 62.5 g (0.5 mol) |
| --- | --- | --- |
| (2) Aqueous phase: | Xylene | 62.5 g |
| | Barium hydroxide (with 8 molecules) | 94.7 g (0.3 mol) |
| | Water | 405.3 g |
| (3) Reaction accelerator: | test quantity of each of the cationic surface active agents of this invention | |

Reaction temperature: 50° C. (constant)
Stirring rate: 1,500 r.p.m.
(2) Test apparatus
Same as used in Example 29.
(3) Calculation of 2-chlorobutadiene formation rate
Determined in the same way as Example 29.
The test results are shown in Table 3.

TABLE 3

2-Chlorobutadiene formation rate in xylene solution-barium hydroxide suspension system of 3,4-dichlorobutene-1

| Sample added | Amount (g) added per 62.5 g 3,4-dichloro-butene-1 | 2-Chlorobuta-diene formation rate after 30-minute treatment at 50° C. | 2-Chlorobuta-diene formation rate after 60-minute treatment at 50° C. |
| --- | --- | --- | --- |
| Blank test (no additive) | — | 0.09% | 1.9% |
| Cationic surface active agent synthesized in Example 1 | 0.05 | 11.0 | 18.0 |
| Cationic surface active agent synthesized in Example 1 | 0.40 | 56.3 | 78.0 |
| Cationic surface active agent synthesized in Example 2 | 0.05 | 12.1 | 18.1 |
| Cationic surface active agent synthesized in Example 2 | 0.50 | 58.2 | 72.3 |
| Cationic surface active agent synthesized in Example 3 | 0.05 | 13.2 | 20.0 |
| Cationic surface active agent synthesized in Example 3 | 0.40 | 61.8 | 79.8 |
| Cationic surface active agent synthesized in Example 4 | 0.10 | 9.9 | 15.6 |
| Cationic surface active agent synthesized in Example 4 | 0.80 | 50.0 | 70.0 |
| Cationic surface active agent synthesized in Example 13 | 0.05 | 11.0 | 17.7 |
| Cationic surface active agent synthesized in Example 13 | 0.40 | 54.9 | 77.7 |
| Cationic surface active agent synthesized in Example 14 | 0.05 | 13.0 | 19.9 |
| Cationic surface active agent synthesized in Example 14 | 0.50 | 60.9 | 78.0 |
| Cationic surface active agent synthesized in Example 15 | 0.05 | 11.0 | 17.9 |
| Cationic surface active agent synthesized in Example 15 | 0.50 | 56.0 | 77.2 |
| Cationic surface active agent synthesized in Example 16 | 0.05 | 10.3 | 16.9 |
| Cationic surface active agent synthesized in Example 16 | 0.80 | 57.1 | 77.0 |
| Cationic surface active agent synthesized in Example 17 | 0.03 | 10.0 | 15.0 |
| Cationic surface active agent synthesized in Example 17 | 0.30 | 51.1 | 72.2 |
| Cationic surface active agent synthesized in Example 18 | 0.04 | 11.2 | 16.0 |
| Cationic surface active agent synthesized in Example 18 | 0.50 | 52.0 | 73.3 |
| Dodecyltrimethylammonium=chloride | 0.10 | 2.9 | 4.6 |
| Dodecyltrimethylammonium=chloride | 1.00 | 10.1 | 29.2 |
| 1,11-Di{methyl=di(2-hydroxyethyl)=ammonium}undecane=dichloride | 0.10 | 1.1 | 2.3 |
| 1,11-Di{methyl=di(2-hydroxyethyl)=ammonium}undecane=dichloride | 1.00 | 3.6 | 4.7 |

EXAMPLE 31

The reaction-promoting effect of the cationic surface active agents of this invention is shown here by taking the reaction for synthesizing 2-chlorobutadiene from 3,4-dichlorobutene-1 as in the case of Example 29. 3,4-dichlorobutene-1 alone was used as organic phase. The test method is as follows:

(1) Test conditions
Reaction molar ratio and proportions of the materials charged:

| (1) Organic phase: | 3,4-dichlorobutene-1 | 62.5 g (0.5 mol) |
| --- | --- | --- |
| (2) Aqueous phase: | Sodium hydroxide | 22 g (0.55 mol) |

| | | |
| --- | --- | --- |
| | Water | 78 g |
| (3) Reaction accelerator: | Test quantity of each of the cationic surface active agents of this invention tested. | |

Reaction temperature: 60° C. (constant)
Stirring rate: 1,200 r.p.m.
(2) Test apparatus
Same as used in Example 29.
(3) Calculation of 2-chlorobutadiene formation rate
Determined in the same way as in Example 29.
(4) Determination of TOC in aqueous phase
Automatic TOC analyzer TOC-H-6 manufactured by Toray Industries Inc. was used.
The test results are shown in Table 4.

TABLE 4

2-Chlorobutadiene formation rate in 3,4-dichlorobutene-1-sodium hydroxide solution system

| Sample added | Amount (g) added per 62.5 g of 3,4-dichloro-butene-1 | 2-Chlorobuta-diene formation rate after 60-minute treatment at 60° C. | TOC in aqueous phase after 60-minute treatment at 60° C. |
|---|---|---|---|
| Blank test (no additive) | — | 5.8% | 100 ppm |
| Cationic surface active agent synthesized in Example 1 | 0.30 | 98.5 | 200 |
| Cationic surface active agent synthesized in Example 2 | 0.35 | 96.2 | 143 |
| Cationic surface active agent synthesized in Example 3 | 0.25 | 97.8 | 113 |
| Cationic surface active agent synthesized in Example 4 | 0.30 | 94.2 | 109 |
| Cationic surface active agent synthesized in Example 13 | 0.35 | 94.3 | 140 |
| Cationic surface active agent synthesized in Example 14 | 0.50 | 94.0 | 110 |
| Cationic surface active agent synthesized in Example 15 | 0.40 | 90.2 | 211 |
| Cationic surface active agent synthesized in Example 16 | 0.50 | 91.1 | 254 |
| Cationic surface active agent synthesized in Example 17 | 0.40 | 90.0 | 232 |
| Cationic surface active agent synthesized in Example 18 | 0.50 | 91.2 | 152 |
| Dodecyltrimethylammonium=chloride | 0.40 | 68.2 | 1047 |
| 1,11-Di{methyl=di(2-hydroxyethyl)=ammonium}undecane=dichloride | 0.40 | 31.1 | 1580 |

EXAMPLE 32

Shown below is the yield-improving effect of the cationic surface active agents of this invention in an alkaline pulp production process. The test method and test results are as follows.

(1) Test method 700 g of broadleaf wood chips were charged into a 4-liter autoclave, to which was added a digesting solution was then further added with a test quantity of each of the cationic surface active agents synthesized in Examples 1–27 and was digested at 155° C. for 75 minutes.

(2) Results

Shown in Table 5.

TABLE 5

Effect of cationic surface active agents in alkaline pulp production process

| Sample added | Amount added per 100 parts by weight of bone-dry chips | Digestion yield | Value k* |
|---|---|---|---|
| Blank test (no additive) | — | 53.0% | 78 |
| Cationic surface active agent synthesized in Example 1 | 0.03 | 53.8 | 51 |
| Cationic surface active agent synthesized in Example 2 | 0.04 | 53.7 | 54 |
| Cationic surface active agent synthesized in Example 3 | 0.03 | 53.8 | 52 |
| Cationic surface active agent synthesized in Example 4 | 0.04 | 53.7 | 54 |
| Cationic surface active agent synthesized in Example 5 | 0.05 | 53.6 | 59 |
| Cationic surface active agent synthesized in Example 6 | 0.04 | 53.6 | 58 |
| Cationic surface active agent synthesized in Example 7 | 0.10 | 53.5 | 60 |
| Cationic surface active agent synthesized in Example 8 | 0.10 | 53.5 | 61 |
| Cationic surface active agent synthesized in Example 9 | 0.08 | 53.5 | 59 |
| Cationic surface active agent synthesized in Example 10 | 0.05 | 53.6 | 59 |
| Cationic surface active agent synthesized in Example 11 | 0.10 | 53.5 | 61 |
| Cationic surface active agent synthesized in Example 12 | 0.10 | 53.6 | 60 |
| Cationic surface active agent synthesized in Example 13 | 0.03 | 53.7 | 54 |
| Cationic surface active agent synthesized in Example 14 | 0.04 | 53.7 | 55 |
| Cationic surface active agent synthesized in Example 15 | 0.04 | 53.7 | 52 |

TABLE 5-continued

Effect of cationic surface active agents in alkaline pulp production process

| Sample added | Amount added per 100 parts by weight of bone-dry chips | Digestion yield | Value k* |
|---|---|---|---|
| Cationic surface active agent synthesized in Example 16 | 0.03 | 53.7 | 52 |
| Cationic surface active agent synthesized in Example 17 | 0.03 | 53.8 | 51 |
| Cationic surface active agent synthesized in Example 18 | 0.03 | 53.8 | 53 |
| Cationic surface active agent synthesized in Example 19 | 0.03 | 53.7 | 59 |
| Cationic surface active agent synthesized in Example 20 | 0.09 | 53.6 | 58 |
| Cationic surface active agent synthesized in Example 21 | 0.10 | 53.5 | 61 |
| Cationic surface active agent synthesized in Example 22 | 0.03 | 53.7 | 60 |
| Cationic surface active agent synthesized in Example 23 | 0.03 | 53.6 | 60 |
| Cationic surface active agent synthesized in Example 24 | 0.03 | 53.6 | 61 |
| Cationic surface active agent synthesized in Example 25 | 0.03 | 53.6 | 59 |
| Cationic surface active agent synthesized in Example 26 | 0.03 | 53.6 | 60 |
| Cationic surface active agent synthesized in Example 27 | 0.04 | 53.5 | 61 |
| Dodecyltrimethylammonium=chloride | 0.10 | 53.0 | 71 |
| 1,11-Di{methyl=di(2-hydroxyethyl)=ammonium}undecane=dichloride | 0.10 | 53.0 | 73 |

(Note)
*The lower the k value, the greater is the amount of lignin extracted.

It is evident from the foregoing that the N- and/or N'-hydroxyphenethyl-substituted N,N'-long chain alkylene type cationic surface active agents according to this invention have far higher catalytic activity then the other types of cationic surface active agents, and also the results of TOC determination indicate less release of the agent into the alkaline solutions. Owing to these properties, the cationic surface active agents of this invention are minimized in wastage in the course of production processes, resulting in an elevated industrial utility and limited influence to environmental pollution. Also, if desired, the cationic surface active agents of this invention may be used in combination with other additives in their use processes.

What is claimed is:

1. A compound having a quaternary ammonium structure represented by the following general formula I:

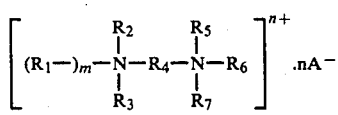

(wherein $R_1$ is hydrogen, or alkyl or hydroxyalkyl having 1-8 carbons, hydroxypolyoxyalkyl having 2-8 carbons, alkylphenyl or phenylalkyl having 7-8 carbons, phenyl, methylbenzyl or glycidyl; $R_2$, $R_3$, $R_5$, $R_6$ and $R_7$ are each alkyl or hydroxyalkyl of 1-8 carbons, hydroxypolyoxyalkyl of 2-8 carbons, alkylphenyl or phenylalkyl of 7-8 carbons, phenyl, methylbenzyl or glycidyl; $R_4$ is an alkylene or polyoxyalkylene group having 6-24 carbon atoms in total; m is 0 or 1; n is 1 or 2; and at least one of $R_1$, $R_2$, $R_3$, $R_5$, $R_6$ and $R_7$ is a hydroxyphenethyl group; $A^-$ is an anion of halide or an organic or inorganic oxyacid residue).

2. The compound according to claim 1, which is a hydrochloric acid neutralized substance of (methyl=2-hydroxyphenethyl)aminoundencyl=methyl=2-hydroxyethyl=2-hydroxyphenethyl=ammonium=chloride.

3. The compound according to claim 1, which is 1,11-di(methyl=2-hydroxyethyl=2-hydroxyphenethyl=ammonium)undecane=dichloride.

4. The compound according to claim 1, which is a hydrochloric acid neutralized substance of (benzyl=2-hydroxyphenethyl)aminoundecyl=benzyl=2-hydroxyethyl=2-hydroxyphenethyl=ammonium=chloride.

5. The compound according to claim 1, which is 1,11-di(benzyl=2-hydroxyethyl=2-hydroxyphenethyl=ammonium)undecane=dichloride.

6. The compound according to claim 1, which is 1,12-di(methyl=2-hydroxyethyl=2-hydroxyphenethyl=ammonium)dodecane=dichloride.

7. The compound according to claim 1, which is 1,12-di(benzyl=2-hydroxyethyl=2-hydroxyphenethyl=ammonium)dodecane=dibromide.

8. The compound according to claim 1, which is 1,17-di(benzyl=2-hydroxyethyl=2-hydroxyphenethyl=ammonium)hexaoxyethylene=dichloride.

9. The compound according to claim 1, which is 1,17-di(di(2-hydroxyethyl)=2-hydroxyphenethyl=ammonium)hexaoxyethylene=dichloride.

10. The compound according to claim 1, which is a hydrobromic acid neutralized substance of (benzyl=2-hydroxyphenethyl)aminododecyl=benzyl=2-hydroxyethyl=2-hydroxystyryl=ammonium=bromide.

11. The compound according to claim 1, which is a hydrochloric acid neutralized substance of (2-hydroxyethyl=2-hydroxyphenethyl)aminoethyltetraoxyethyleneoxyethyl=di(2-hydroxyethyl)=2-hydroxyphenethyl=ammonium=chloride.

* * * * *